United States Patent [19]

Fraij et al.

[11] Patent Number: 5,726,051

[45] Date of Patent: Mar. 10, 1998

[54] TRANSGLUTAMINASE GENE

[75] Inventors: Bassam M. Fraij, Payne; Paul J. Birckbichler, Oklahoma City; Manford K. Patterson, Jr.; Robert A. Gonzales, both of Ardmore, all of Okla.

[73] Assignee: Oklahoma Medical Research Foundation, Oklahoma City, Okla.

[21] Appl. No.: 247,902

[22] Filed: May 23, 1994

Related U.S. Application Data

[63] Continuation-in-part of Ser. No. 126,119, Sep. 23, 1993, abandoned, which is a continuation of Ser. No. 969,702, Nov. 3, 1992, abandoned.

[51] Int. Cl.[6] .............................. C12N 9/10; C12N 15/54
[52] U.S. Cl. .................................... 435/193; 536/23.2
[58] Field of Search ............................................. 435/193

[56] References Cited

U.S. PATENT DOCUMENTS 4,929,554  5/1990  Goeddel et al. ....................... 435/172.3

FOREIGN PATENT DOCUMENTS 0268772  6/1988  European Pat. Off. .
WO9106553  5/1991  WIPO .
WO9212238  7/1992  WIPO .

OTHER PUBLICATIONS

Fraij, et al., "A Novel Human Tissue Transglutaminase Homologue from Erythroleukemia Cells," *Third International Conference on Transglutaminase and Protein Crosslinking Reactions*, Jun. 7–10, 1992, U.S.A.

Folk, "Transglutaminases," *Ann Rev Biochem* 49:517–31 (1980).

Davis, et al., "Retinoic acid–induced expression of tissue transglutaminase in human promyelocytic leukemia (HL–60) cells," *J Biol Chem* 260:5166–5174 (1985).

Suedhoff, et al., "Differential expression of transglutaminase in human erythroleukemia cells in respone to retinoic acid," *Cancer Research* 50:7830–7834 (1990).

Gentile, et al., "Isolation and Characterization of cDNA clones to mouse macrophage and human endothelial cell tissue transglutaminases," *J Biol Chem* 266:478–483 (1991).

Fesus, et al., "Apoptotic hepatocytes become insoluble in detergents and chaotropic agents as a result of transglutaminase action," *FEBS Letters* 245:150–154 (1989) Amsterdam, Netherlands.

Birnboim, "Rapid extraction of high molecular weight RNA from cultured cells and granulocytes for Northern analysis," *Nucleic Acids Res* 16:1487–1497 (1988) Oxford, England.

Aviv, et al., "Purification of biologically active globin messenger RNA by chromatography on oligothymidylic acid–cellulose," *Proc Natl Acad Sci USA* 69:1408–1412 (1972).

Ausubel, et al., "Analysis of RNA by Northern hybridization", *Current Protocols in Molecular Biology*, pp. 4.9.1–4.9.8 (1987), John Wiley & Sons, New York, NY.

Maniatis, et al., "Large–scale isolation of plasmid DNA," *Molecular Cloning: A Laboratory Manual*, Cold Spring Harbor Laboratory, Cold Spring Harbor, NY, pp. 86–91 (1982).

Titus, D.E. (Ed), "Nucleic acid detection, purification and labeling," *Promega Protocols and Applications Guide*, 2nd Ed., pp. 138–139, Promega Corp., Madison, WI (1991).

McClung, et al., "Purification of plasmid DNA by fast protein liquid chromatography on Superose 6 preparative grade," *Anal Biochem* 177:378–382 (1989).

Buck, et al., "A general method for quantitative PCR analysis of mRNA levels for members of gene families: application to $GABA_A$ receptor subunits," *BioTechniques* 11:636–641 (1991).

Marchuk, et al., "Construction of T–vectors, a rapid and general system for direct cloning of unmodified PCR products," *Nucleic Acids Res* 19:1154 (1990) Oxford, England.

Ikura, et al., "Amino acid sequence of guinea pig liver transglutaminase from its cDNA seqence", *Biochem* 27:2898–2905 (1988).

Korsgren, et al., "Complete amino acid sequence and homologies of human erythrocyte membrane protein band 4.2," *Proc Natl Acad Sci USA* 87:613–617 (1990).

Thomazy,et al., "Differential expression of tissue transglutaminase in human cells—An immunohistochemical study," *Cell Tissue Res* 255:215–224 (1989), Berlin, Germany.

Sung, et al., "Molecular cloning of human protein 4.2: A major component of the erythrocyte membrane," *Proc Natl Acad Sci USA* 87:955–959 (1990).

Williams–Ashman, et al., "Transglutaminases in mammalian reproductive tissues and fluids: relation to polyamine metabolism and semen coagulation," *Advances in Enzyme Regulation*, George Weber, ed., 18:239–258, New York (1980).

Birckbichler, et al. "Differential transglutaminase distribution in normal rat liver and rat hepatoma," *Cancer Research* 36:2911–2914 (1976).

Chiocca, et al., "Regulation of tissue transglutaminase gene expression as a molecular model for retinoid effects on proliferation and differentiation," *J Cell Biochem* 39:293–304 (1989).

Kim, et al., "The complete amino acid sequence of the human transglutaminase K enzyme deduced from the nucleic acid sequences of cDNA clones," *J Biol Chem* 266:536–539 (1991).

(List continued on next page.)

*Primary Examiner*—Robert A. Wax
*Assistant Examiner*—Eric Grimes
*Attorney, Agent, or Firm*—Sidley & Austin

[57] ABSTRACT

The present invention relates to a 1.9 kb cDNA and new tissue transglutaminase protein encoded thereby. The cDNA was obtained from reverse transcription of mRNA isolated from retinoic-acid treated HEL cells. The invention also relates to vectors and expression systems to produce the new tissue transglutaminase as well as the recombinantly-produced enzyme protein.

4 Claims, 3 Drawing Sheets

OTHER PUBLICATIONS

Knight, et al., "The existence of an inactive form of transglutaminase within metastasising tumours," *Biochim Biophys Acta* 1053:13–20 (1990), Amsterdam, Netherlands.

Birckbichler, et al., "Cellular transglutaminase, growth, and transformation," *Ann NY Acad Sci* 312:354–365 (1978).

Seitz, et al., "Purification and molecular characteristic of a secretory transglutaminase from coagulating gland of the rat," *Biochim Biophys Acta* 1078:139–146 (1991), Amersterdam, Netherlands.

Ichinose, et al., "Amino acid sequence of the b subunit of human Factor XIII, a protein composed of ten repetitive segments," *Biochemistry* 25:4633–4638 (1986).

Fraij, et al., "A retinoid acid–inducible mRNA from human erythroleukemia cells encodes a novel tissue transglutaminase homologue," *J Biol Chem* 267:22616–22623 (1992).

Gentile et al., "Molecular cloning and sequence analysis of cDNA for a retinoic acid–inducible tissue transglutanminase from human umbilical vein endothelial cells," *2nd International Conference on Transglutaminases and Protein Cross–linking Reactions*, Jun. 24–28, 1990, abstract.

Saydak, et al., "cDNA cloning of mouse macrophage tissue transglutaminase," *FASEB J* 3:A1209, abstract 5708 (1989).

Gentile et al., "Isolation and characterization of cDNA and genomic clones of human endothelial cell transglutaminase," *J Cell Biol* 109:198a, abstract 1068 (1989).

Fesus et al., Adv. Exp. Med. Biol. 231:119–134 (1988).

|      |            |            |            |            |            |            |
|-----:|------------|------------|------------|------------|------------|------------|
|    1 | caggcgtgac | gccagttcta | aatcttgaaa | cagaacaaaa | cttcaaagta | caccaaaata |
|   61 | gaacctcctt | aaagcataaa | tctcacggag | ggtctcgccg | ccagtggaag | gagccaccgc |
|  121 | ccccgcccga | ccatggccga | ggagctggtc | ttagagaggt | gtgatctgga | gctggagacc |
|  181 | aatggccgag | accaccacac | ggccgacctg | tgccgggaga | agctggtggt | gcgacggggc |
|  241 | cagcccttct | ggctgaccct | gcactttgag | ggccgcaact | acgaggccag | tgtagacagt |
|  301 | ctcaccttca | gtgtcgtgac | cggcccagcc | cctagccagg | aggccgggac | caaggcccgt |
|  361 | tttccactaa | gagatgctgt | ggaggagggt | gactggacag | ccaccgtggt | ggaccagcaa |
|  421 | gactgcaccc | tctcgctgca | gctcaccacc | ccggccaacg | cccccatcgg | cctgtatcgc |
|  481 | ctcagcctgg | aggcctccac | tggctaccag | ggatccagct | ttgtgctggg | ccacttcatt |
|  541 | ttgctcttca | acgcctggtg | cccagcggat | gctgtgtacc | tggactcgga | agaggagcgg |
|  601 | caggagtatg | tcctcaccca | gcagggcttt | atctaccagg | gctcggccaa | gttcatcaag |
|  661 | aacatacctt | ggaattttgg | gcagtttgaa | gatgggatcc | tagacatctg | cctgatcctt |
|  721 | ctagatgtca | accccaagtt | cctgaagaac | gccggccgtg | actgctcccg | ccgcagcagc |
|  781 | cccgtctacg | tgggccgggt | ggtgagtggc | atggtcaact | gcaacgatga | ccagggtgtg |
|  841 | ctgctgggac | gctgggacaa | caactacggg | gacggcgtca | gccccatgtc | ctggatcggc |
|  901 | agcgtggaca | tcctgcggcg | ctggaagaac | cacggctgcc | agcgcgtcaa | gtatggccag |
|  961 | tgctgggtct | tcgccgccgt | ggcctgcaca | gtgctgaggt | gcctgggcat | ccctacccgc |
| 1021 | gtcgtgacca | actacaactc | ggcccatgac | cagaacagca | accttctcat | cgagtacttc |
| 1081 | cgcaatgagt | ttggggagat | ccaggtgac | aagagcgaga | tgatctggaa | cttccactgc |
| 1141 | tgggtggagt | cgtggatgac | caggccggac | ctgcagccgg | ggtacgaggg | ctggcaggcc |
| 1201 | ctggacccaa | cgccccagga | gaagagcgaa | gggacgtact | gctgtggccc | agttccagtt |
| 1261 | cgtgccatca | aggagggcga | cctgagcacc | aagtacgatg | cgccctttgt | ctttgcggag |
| 1321 | gtcaatgccg | acgtggtaga | ctggatccag | caggacgatg | ggtctgtgca | caaatccatc |
| 1381 | aaccgttccc | tgatcgttgg | gctgaagatc | agcactaaga | gcgtgggccg | agacgagcgg |
| 1441 | gaggatatca | cccacaccta | caaatacca | gagggtcct | cagaggagag | ggaggccttc |
| 1501 | acaagggcga | accacctgaa | caaactggcc | gagaaggagg | agacagggat | ggccatgcgg |
| 1561 | atccgtgtgg | gccagagcat | gaacatgggc | agtgactttg | acgtctttgc | ccacatcacc |
| 1621 | aacaacaccg | ctgaggagta | cgtctgccgc | ctcctgctct | gtgcccgcac | cgtcagctac |
| 1681 | aatgggatct | tggggcccga | gtgtggcacc | aagtacctgc | tcaacctcaa | cctggagcct |
| 1741 | ttctctggta | aagccctgtg | ttcctggagc | atttgttgac | cgccaactga | caacatgcta |
| 1801 | ggtagtgacc | taaccactta | gcatgtgtga | tttcacccca | cagacactta | catggcgctg |
| 1861 | actctggggc | aggccctgtc | ctaagcactt | tataaatatc | aacccactta |            |

FIG. 1

TRANSGLUTAMINASE GENE

CROSS REFERENCE TO RELATED APPLICATION

This is a continuation-in-part of U.S. application Ser. No. 08/126,119 filed Sep. 23, 1993, which is a continuation of U.S. application Ser. No. 07/969,702 filed Nov. 3, 1992, both now abandoned.

TECHNICAL FIELD OF THE INVENTION

This invention relates to transglutaminase enzymes, genes encoding transglutaminase enzymes, and recombinant production of transglutaminase enzymes.

BACKGROUND OF THE INVENTION

Transglutaminases are a family of enzymes which catalyze the formation of simple ε-(γ-glutamyl) lysine isopeptide bonds in proteins. The enzymes function by catalyzing an acyl-transfer reaction in which γ-carboxamide groups on peptide-bound glutamine residues serve as the acyl donors. Although the donor substrate is primarily glutamine, the transglutaminases differ in their specificity for acceptor substrates. The ε-amino groups of peptide-bound lysine residues play an important role as acceptor substrates.

In general, transglutaminases are involved in protein cross-linking. Some examples of transglutaminases include activated Factor XIII, epidermal transglutaminase, and prostate transglutaminase. Factor XIII stabilizes fibrin clots during coagulation by cross-link formation. Epidermal transglutaminase is involved in cornified envelope formation during epithelial cell differentiation. Prostate transglutaminase is involved in vaginal plug formation in rodents. For a general discussion of transglutaminases see Folk, "Transglutaminases", *Ann Rev Biochem* 49:517–531 (1980). Additionally, there is a tissue or cellular form of transglutaminase found in nearly all tissues. Although the biological function of this tissue transglutaminase (TGase) is unclear, for years there has been some evidence that the tissue transglutaminase enzyme plays a role in cell differentiation. This was learned primarily through work involving retinoic acid induction of cell differentiation.

Retinoic acid (RA) exerts profound effects on the differentiation of many cell types. In promyelocytic leukemia cell line HL-60, it was shown that retinoic acid induced cellular differentiation and tissue or cellular transglutaminase messenger RNA (mRNA). Davies, et al., "Retinoic acid-induced expression of tissue transglutaminase in human promyelocytic leukemia (HL-60) cells," *J Biol Chem* 260:5166–5174 (1985). A similar effect was found in human erythroleukemia cells. Suedhoff, et al., "Differential expression of transglutaminase in human erythroleukemia cells in response to retinoic acid," *Cancer Research* 50:7830–7834 (1990), incorporated herein by reference.

The RA-associated differentiation of human erythroleukemia (HEL) cells has been used to study the regulation of transglutaminase-related genes. In previous work (Suedhoff, et al.), Northern blots of polyadenylated RNA isolated from retinoic acid-treated HEL cells were hybridized with a cellular transglutaminase-specific sequence. An increase in two distinct messenger RNA populations within the first 12 hours of exposure to retinoic acid was revealed. One consisted of mRNA of 4.0 kb. The other consisted of mRNA of 7.4 kb.

The identification of these two populations of mRNA was made using a 2.0 kilobase fragment containing only the coding region of a 3.5-kilobase cDNA for tissue transglutaminase which had been cloned into a pBluescript SK(–) vector. The vector was received from Dr. Peter Davies, Houston, Tex. Dr. Davies' lab had previously isolated and characterized 3.6–3.7 kilobase cDNA clones to human endothelial cell tissue transglutaminases. The sequence for Dr. Davies' cDNA was reported in Gentile, et al., "Isolation and characterization of cDNA clones to mouse macrophage in human endothelial cell tissue transglutaminases," *J Biol Chem* 266:478–483 (1991), incorporated herein by reference.

Prior work in identifying transglutaminase enzymes nonetheless left a need to identify and characterize new transglutaminase enzymes. Toward this end, a fragment of Dr. Davies' cDNA for tissue transglutaminase was used in a Northern blotting screen. However, a shorter fragment of the human tissue transglutaminase cDNA was used—i.e., 2.0 kb which contained only the coding region to avoid non-specific hybridization. Using the shorter fragment, two mRNA populations in the cell extracts—4.0 kb and 1.9 kb—were identified. The 1.9 kb cDNA obtained and the protein encoded thereby is the subject of the present invention and is hereinafter referred to as "TGase-H."

SUMMARY OF THE INVENTION

In one aspect, the present invention provides a novel transglutaminase gene.

In a further aspect, the present invention provides a vector comprising DNA encoding a novel human tissue transglutaminase.

In another aspect, the present invention provides a bacterial expression system for producing the novel transglutaminase.

In yet another aspect, the present invention provides a process for producing the novel transglutaminase.

In a further aspect, the present invention provides a recombinantly produced novel transglutaminase.

BRIEF DESCRIPTION OF THE DRAWINGS

FIG. 1 is the nucleic acid sequence of TGase-H cDNA (SEQ ID NO:1).

DETAILED DESCRIPTION

Figure 2:
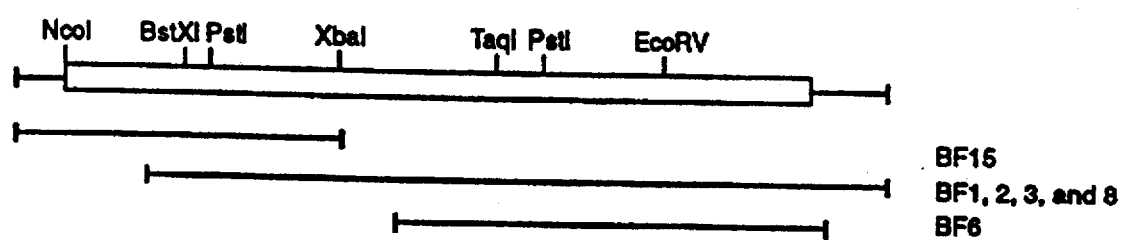
FIG. 2 is a schematic representation of the human TGase-H cDNA and the restriction map.

A full-length cDNA that encodes a novel tissue transglutaminase homologue (TGase-H) has now been found and characterized. A deposit of clone TGase-H was made with the American Type Culture Collection ("ATCC"), 12301 Parklawn Drive, Rockville, Md. 20852 on Jun. 4, 1993. The ATCC designation for clone TGase-H is "75478."

Northern blot analysis of RA-treated HEL cells revealed the novel TGase-H mRNA (1.9 kb). The identification and characterization of any new related mRNA is important for further studies of cellular TGase function(s), to discern what functional role the new protein might perform in the cell and because a new transglutaminase protein would have potential for commercial applications such as clot formation.

Two mRNA species code for TGase-H, one consisting of 1910 nucleotides as shown in FIG. 1 and SEQ ID NO:1 and one consisting of 1840 nucleotides (not shown) not including the poly(A) tail. This indicates a difference in the polyadenylation sites. It is recognized that a large number of genes in higher eukaryotes produce multiple mRNAs because of alternative mRNA processing. The mechanism of such processing, however, remains unclear.

The cDNAs of cellular TGase and the novel TGase-H disclosed herein were determined to be very nearly identical in the common coding region where only ten base changes were found. These changes possibly were a combination of polymorphisms and ambiguities in sequencing. Most of the base changes found in the cDNA for TGase-H were silent with the ten changes found in the common coding region resulting in only five amino acids that were changed. Even though TGase-H is considerably shorter and displays different enzyme kinetics, all of the above evidence suggests that the new protein is likely to be a TGase homologue.

been reported in humans. The amino acid sequence of TGase-H contains about 78% of the cellular TGase $NH_2$-terminal sequence. The missing 22% of the amino acids from the carboxyl end had no significant effect on the calculated isoelectric point (Table I). It is likely that TGase-H is an isoform of the cellular TGase. This assumption is based on the complete conservation of the active site region, the putative $Ca^{2+}$-binding site, and the close total net charges as judged by the isoelectric points. More importantly it has been shown (see Example 6) that TGase-H is an active, functional enzyme by a test developed to assay cross-linking enzymes. See Lorand et al., Anal Biochem 50:623 (1972). This indicates that the major function of TGase-H in isopeptide cross-linking would not be significantly affected.

TABLE I

| Amino Acid | Human TGase-H | Human cellular TGase | Rat CGS-TGase | Guinea pig liver TGase | Human factor XIIIa | Human protein 4.2 |
|---|---|---|---|---|---|---|
| Asx | 62 | 72 | 58 | 78 | 87 | 56 |
| Glx | 62 | 83 | 57 | 77 | 75 | 86 |
| Ser | 37 | 40 | 47 | 43 | 46 | 45 |
| Gly | 43 | 51 | 36 | 57 | 50 | 47 |
| His | 11 | 13 | 8 | 12 | 14 | 12 |
| Arg | 32 | 39 | 24 | 40 | 45 | 43 |
| Thr | 29 | 35 | 36 | 31 | 45 | 43 |
| Ala | 33 | 40 | 30 | 45 | 37 | 56 |
| Pro | 22 | 32 | 26 | 32 | 33 | 34 |
| Tyr | 19 | 23 | 18 | 24 | 29 | 16 |
| Val | 41 | 57 | 40 | 60 | 70 | 49 |
| Met | 9 | 11 | 19 | 9 | 19 | 9 |
| Cys | 19 | 20 | 19 | 17 | 9 | 15 |
| Ile | 24 | 32 | 39 | 34 | 39 | 31 |
| Leu | 49 | 69 | 52 | 69 | 48 | 79 |
| Phe | 22 | 25 | 30 | 23 | 32 | 24 |
| Trp | 14 | 13 | ND | 10 | 15 | 14 |
| Lys | 20 | 32 | 53 | 29 | 38 | 32 |
| pI | 4.84* | 4.95* | 7.6 | 4.92 | 5.88 | 7.96 |
| Calculated molecular mass (kD) | 61.7 | 77.3 | ND | 76.6 | 83.1 | 76.9 |
| SDS molecular mass (kD) | 63 | 82 | 65 | 77 | 75 | 72 |
| Ref. | | Gentile[1] | Seitz[2] | Ikura[3] | Ichinose[4] | Korsgren[5] |

*Amino acid composition pI values and calculated molecular masses were computed from the deduced amino acid sequences.
Prior Art references:
[1]Gentile, et al., j. Biol. Chem., 266:478-483 (1991).
[2]Seitz, et al., Biochem. Biophys. Acta, 1078:139-146 (1991).
[3]Ikura, et al., Biochemistry, 27:2898-2905 (1988).
[4]Ichinose, et al., Biochemistry, 25:6900-6906 (1986).
[5]Korsgren, et al., Proc. Natl. Acad. Sci. U.S.A., 87:613-617 (1990).

Comparison of the deduced amino acid sequences for cellular TGase and TGase-H revealed the absence of about 147 amino acids from the carboxyl terminus of the cellular TGase in the TGase-H. The absence of these amino acids from the homologue may attribute to some differences in the function(s) of TGase-H. An example of where a short end sequence resulted in some functional loss was found in a calmodulin-binding protein (calspermin). Ono, et al., J Biol Chem 259:9011-9016 (1984). Also, alternative splicing produced two mRNAs that differed at their 3' ends in the endoplasmic riticulum Ca-ATPase. The carboxyl end of the protein products of these mRNAs were different and each was found to be cardiac or smooth muscle specific. Lytton, et al., J Biol Chem 263:15024-15031 (1988).

Figure 3:
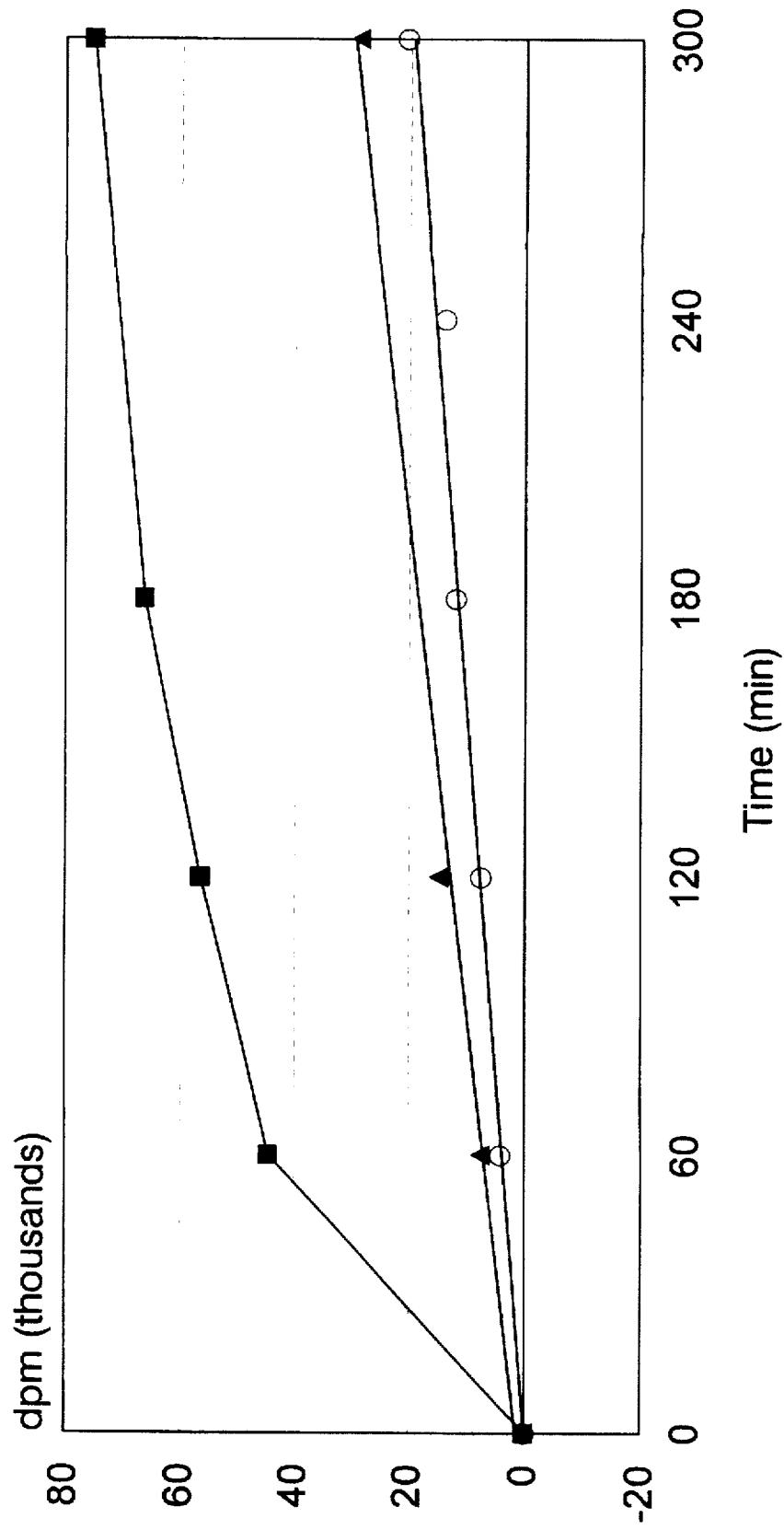
FIG. 3 is a graphic representation of the enzyme kinetics of TGase-H versus guinea pig transglutaminase (TGase), wherein open circles represent 3 micrograms TGase-H; closed triangles represent 6 micrograms TGase-H; and closed squares represent 9 micrograms guinea pig TGase.

The deduced amino acid sequences and content showed that TGase-H has a unique size with a molecular mass of 63 kD. To our knowledge, no transglutaminase of this size has Interestingly, however, TGase-H has been shown to exhibit distinctly different kinetics than some other transglutaminases as demonstrated by FIG. 3 and shown in Table II. These both represent results of $C^{14}$-putrescine incorporation into dimethylated casein, which is a test developed to assay the activity of cross-linking enzymes.

TABLE II

| Kinetics of TGase-H vs Guinea Pig TGase | | | |
|---|---|---|---|
| | Incorporation of Radioactive Putrescine into Dimethylated Casein (dpm) | | |
| Time (min) | TGH (3 µg) | TGH (6 µg) | Guinea pig TGase (9 µg) |
| 0 | 0 | 0 | 0 |
| 60 | 4,218 | 7,556 | 45,599 |
| 120 | 7,548 | 14,755 | 56,567 |

TABLE II-continued

Kinetics of TGase-H vs Guinea Pig TGase

| Time (min) | Incorporation of Radioactive Putrescine into Dimethylated Casein (dpm) | | |
|---|---|---|---|
| | TGH (3 µg) | TGH (6 µg) | Guinea pig TGase (9 µg) |
| 180 | 11,949 | — | 66,293 |
| 240 | 13,798 | — | — |
| 300 | 20,456 | 28,846 | 75,160 |

See Lorand, et al., "A filter paper assay for transaminating enzymes using radioactive amine substrates," *Analytical Biochemistry* 50:623 (1972), incorporated herein by reference. TGase-H exhibits a constant rate of cross-linking over an extended period of time (up to 5 hours has been tested). Guinea pig liver transglutaminase, contrastingly, shows activity which incorporates rapidly for about 1.5 hours after which the rate drops off. This unexpected property for TGase-H should prove to be advantageous for the relatively slow process of wound healing. As applied under bandages, other transglutaminases would lose activity relatively quickly, requiring reapplication more frequently. These reproducible assay studies indicate that although TGase-H catalyzes the same reaction, as would be expected due to conservation of the active site and calcium binding site, the absence of about 147 C-terminal amino acids significantly affects its kinetics. The existence of the reading frame for TGase-H mRNA was verified by both in vitro transcription and translation and in vivo expression. The immunoprecipitation of the native TGase-H from the HEL cells showed a protein of similar size (63 kD) as the TGase-H from the in vitro translation product. Therefore, it is likely that TGase-H does not undergo a major glycosylation or other post-translational modifications. Despite the missing amino acids from the carboxyl terminus, the antibodies raised against cellular TGase reacted with TGase-H. This indicates that these amino acids are not required for the binding of antibody.

Several expression vectors were found to be unsuitable for producing the TGase-H protein including pBluescript (Stratagene, La Jolla, Calif.), pSL301, pSE280, and pSE380 (Invitrogen) with the protocols recommended by the manufacturers.

Good expression of TGase-H was accomplished using a new vector (pRSET) from Invitrogen in which a T7 bacterial phage promoter in the vector is used to drive expression in bacteria. The plasmid is usually grown in the presence of T7 RNA polymerase encoded by M13 which is added to the media as described by the supplier (Invitrogen). However a higher level of expression was found when the host cell encoded the T7 polymerase. Although adequate quantities of TGase-H were generated by that procedure, the result was a fusion protein which was largely deposited in inclusion bodies. Attention was therefore focused on other vectors which could produce active native TGase-H.

In vivo expression is accomplished most preferably with a pET vector in BL21 (Novagen) bacterial cells as described in Example 6, although TGase-H was also successfully expressed with a pRSET B vector (Invitrogen) as described above. The expression in both vectors required considerable modification of the recommended protocols. Although many other expression systems may work to produce TGase-H, it has been found that the yield and activity may be increased by the modifications taught herein. These could include other prokaryotic systems or eukaryotic systems with the T7 promoter or another suitable promoter. Viral vectors could be used both in prokaryotic and eukaryotic systems as well. In a preferred embodiment of the in vivo expression of TGase-H according to the invention, the TGase-H cDNA (SEQ ID NO: 1) is incorporated into an appropriate vector, which is then introduced into a suitable host for expression. Preferably, vector pET 14-b or pET 15-b (Novagen) is employed, although any appropriate plasmid or other vector might be used. Although many commercially available vectors including these are provided with protocols by the manufacturer, it was found that to express sufficient amounts of active TGase-H, a novel protocol had to be developed. This novel protocol was used to express the previously described cDNA. A standard protocol for that vector was modified by the addition of yeast extract to the growth media, lowering the assay reaction temperature to about 30° C., and surprisingly by expressing the gene without IPTG induction in one case.

The expression method of the invention produced an active transglutaminase enzyme as shown by radioactive putrescine incorporation into dimethylated casein. The preferred expression method is detailed in Example 6.

Several purification steps can be used to purify active TGase-H. Standard protein purification techniques well known in the art can be used singly or in conjunction with others to purify the TGase-H protein from the bacterial culture. For example, 40% $(NH_4)_2 SO_4$ precipitation; 15% polyethylene glycol (PEG) precipitation, DE-cellulose, (from Whatman Co., Clifton, N.J.) according to supplier's protocols; QA-cellulose, (from Whatman Co.) according to supplier's protocols; CM-cellulose, (from Whatman Co.) according to suppliers's protocols; hydroxylapatite, (from Bio-rad, Hercules, Calif.) according to supplier's protocols; phenyl-sepharose (Pharmacia, Piscataway, N.J.), according to manufacturer's protocols; FPLC and HPLC, in 0.01M Tris pH 7.5, 1 mM EDTA; monoclonal antibody sepharose, (according to Lee, et al., *Preparative Biochem* 16:321-335 (1986); DE Toyo in 0.01M sodium phosphate, pH 6.8; GTP-sepharose column (Sigma) ("affinity column") in 0.01M Tris pH 7.5 have been used.

To confirm the sequence of the bacterial TGase-H enzyme produced, micro-protein sequencing from partially pure TGase-H separated by SDS-PAGE was performed. For fifteen cycles, the N-terminal sequences of TGase-H were identical and matched the deduced amino acid sequence of the reported cDNA. These sequences are:1-Ala 2-Glu 3-Glu 4-Leu 5-Val 6-Leu 7-Glu 8-Arg 9- probably Cys 10-Asp 11-Leu 12-Glu 13-Leu 14-Glu 15-Thr (SEQ ID NO:6).

The human tissue transglutaminase with a molecular weight of about 80 kD has been extensively identified and studied. There are several reports about purification of catalytically active human tissue transglutaminase from different tissues, and all these reports indicated that the transglutaminase activity was found in a single enzyme form of about 80 kD molecular weight. The discovery of a novel human tissue transglutaminase homologue reveals for the first time the existence of a new form with a molecular weight of about 63 kD. The mass production of catalytically active tissue transglutaminase homologue (TGase-H) with a molecular weight of 63 kD in bacteria is illustrated in Example 6. Because it is a smaller protein, large quantities should be produced with the expenditure of less metabolic energy, and it may be less likely to be isolated in inclusion bodies. The enzyme shows substantial stability after several steps of purification, and there was no substantial activity loss after lyophilization.

Different isoforms and isoenzymes are widely found to possess certain tissue specificity. It remains to be shown what specificity the tissue transglutaminase (80 kD) and the TGase-H (63 kD) would have under metabolic and cellular activity. Although the main function of TGases is reportedly to catalyze the formation of ε-(γ-glutamyl) lysine isopeptide bonds, an example of which is the stabilization of a fibrin clot during coagulation as catalyzed by Factor XIIIa, the cellular TGase biological function is not completely understood. There has been some evidence that this enzyme plays a role in a calcium-dependent cross-linking of cell membrane and cytoskeletal proteins. Recent data showed that the enzyme may act in the formation of a cross-linked apoptosis envelope during programmed cell death.

Recent studies also report that tissue TGases are GTP-binding proteins and show GTPase activity, and that TGase's cross-linking activity can be inhibited by GTP. See Achyuthan, K. E., and Greenberg, C. S., (1987) "Identification of a guanosine triphosphate-binding site on guinea pig liver transglutaminase. Role of GTP and calcium ions in modulating activity," *J Biol Chem* 262:1901–1906 (1987), Bergamini, et al., "Inhibition of erythrocyte transglutaminase by GTP," *Biochim Biophys Acta* 916:149–151 (1987), Bergamini, C. M., "GTP modulates calcium binding and cation-induced conformational changes in erythrocyte transglutaminase," *FEBS Lett.*, 239:255–258 (1988). Lee, et al., "GTP hydrolysis by guinea pig liver transglutaminase," *Biochem Biophys Res Commun* 162:1370–1375 (1989). Thus, cellular TGase may function as a multifunctional enzyme. It would be of interest to determine if TGase-H has multi-functional activities.

As discussed above, there are identities among the sequences of the TGase and TGase-H proteins. In the TGase-H protein, the active site region residues 271–312 including cysteine (codon 277) and the potential $Ca^{2+}$-binding region between 446 and 453 amino acids of the cellular TGase are conserved. These two regions were found to be conserved with a high degree of homology among human Factor XIIIa, other TGases, and Protein 4.2. The exception was that alanine instead of cysteine (codon 277) was found at the active site in Protein 4.2.

HEL cells from a naturally occurring tumor expressed both the cellular TGase and the new form of transglutaminase homologue (TGase-H). The mRNA used for obtaining the cDNA of the present invention is present in HEL cells that have not been retinoic acid-induced, but to a much lesser extent and not in amounts sufficient to enable its isolation. The mRNA is greatly increased upon induction of HEL cells with retinoic acid to such an extent as to facilitate its isolation and identification using the method employed herein. Since retinoic acid induces cellular differentiation, the increased level of the mRNA in retinoic acid-induced HEL cells links the tissue transglutaminase of the invention to cellular differentiation. Consequently, the method of isolation indicates that the cDNA of the present invention can be used to design probes of identical sequences for screening cells to monitor differentiation. From the cDNA of the present invention, vectors for inducing cellular differentiation can be made by techniques known to the art.

HEL cells from a naturally-occurring tumor also expressed the tissue transglutaminase of the invention. Expression of the tissue transglutaminase of the invention (TGase-H), then, may also be related to oncogenesis and/or tissue-specific regulation. Accordingly, TGase-H can serve not only as a marker for differentiation, but also tumorigenesis. Further, since TGase-H is lacking about 147 amino acids from the carboxyl terminus of tissue transglutaminase, TGase-H can be used to identify functional domains of the proposed multi-functional tissue transglutaminase enzyme and, concomitantly, diseases related to genetic mutations involving those domains. Probes can also be made from the cDNA of this invention to be used as a scientific tool to identify and isolate as yet undiscovered transglutaminases and proteins with related sequences.

TGase-H may be useful in food preservation. The protein crosslinking activity may be used to form a protective coat on food items such as meats, slowing decay from bacterial damage and dehydration.

Hereinafter, whenever a reference is cited following a discussion of a procedure, the disclosure in that reference is incorporated by reference.

EXAMPLE 1

Isolation of 1.9 kb mRNA

GM06141A (HEL) cells were obtained from the human genetic mutant cell repository (Camden, N.J.) and cultured as described previously. Suedhoff, et al., *Cancer Res* 50:7830–7834 (1990). Total cellular RNA was isolated by an established method. Birnboim, H. C., *Nucleic Acids Res* 16:1487–1497 (1988). The poly(A)$^+$ mRNAs were purified from total RNA by oligo(dT)-cellulose column chromatography. Aviv, et al., *Proc Natl Acad Sci USA* 69:1408–1412 (1972). The poly(A)$^+$ mRNAs coding for tissue transglutaminase (TGase) were screened using human cellular TGase cDNA.

The human cellular TGase cDNA used was a 3.5-kilobase insert cloned into a pBluescript SK(−) vector provided by Dr. Peter Davies, Houston, Tex. After digestion with the restriction enzymes NcoI and MstII, a 2.0-kilobase fragment of this insert was obtained which contained only the coding region of the DNA. Screening of the mRNA was conducted using Northern blot analysis. Four micrograms of total poly(A)$^+$ RNA from each cell line was sized by electrophoresis, transferred to a filter, and hybridized with the TGase coding region probe. Messenger RNA samples were separated by electrophoresis on a 1.2% agarose formaldehyde gel and transferred onto a ZETAPROBE nylon membrane (Bio-Rad) as described previously. Ausubel, et al., (1987), *Current Protocols in Molecular Biology*, Wiley Interscience, New York. The membrane was hybridized at 42° C. overnight in 50% formamide, 0.25M sodium phosphate, pH 7.2, 0.2 mM EDTA, 0.25M sodium chloride, and 3.5% SDS. The blot was washed in 5× SSC, 0.5% SDS for 15 minutes at 42° C., followed by two washes in 1× SSC, 0.5% SDS at 60° C. Two bands of about 4.0 and 1.9 kilobases at a relative abundance of about 3:1 were detected. The 1.9-kb band was regenerated by cutting the band from the formaldehyde sizing gels and passing the extracted mRNA over oligo(dT)-cellulose. That the 1.9 kb fragment was capable of regeneration in this manner indicates the presence of a poly(A) tail. Northern analysis of poly(A)$^+$ mRNA probed with a 0.8-kb noncoding cDNA region of the cellular TGase revealed the 4.0-kb band only. This indicates the absence of the 3' end of the cellular TGase sequences in the 1.9 Kb species and/or eliminates the possibility that a degradation of the 4.0-kb band may lead to a smaller RNA species. The above data illustrate that the 1.9-kb band is a distinct polyadenylated mRNA that hybridizes strongly with the TGase cDNA probe.

EXAMPLE 2

Preparation of cDNA

Ten µg of the 1.9 kb poly(A)$^+$ RNA was primed with oligo(dT) for cDNA and double-stranded cDNA synthesis using the Librarian Kit (Invitrogen, San Diego, Calif.). In order to eliminate the construction of the cellular TGase (4.0) kb cDNA in this library, the double stranded cDNA was fractionated by electrophoresis on 1% low melting agarose (Bethesda Research Laboratories) in TAE buffer (0.04M Tris acetate, 0.0002M EDTA, pH 8.5). cDNA in the range of 1.5–2.0 kb (Library 1) and 2.0–3.0 kb (Library 2) were excised and purified by a standard phenol/chloroform method. The purified double-stranded cDNAs were used to construct two λgt10 phage libraries by using the Librarian Kit (Invitrogen, San Diego, Calif.). *Escherichia coli* (C600) cells were infected with the recombinant phages at $4 \times 10^4$ plaque-forming units/150-mm Petri dish. Nick-translated $^{32}$P labeled 2.0-kb cellular TGase probes were used to screen and rescreen the recombinant clones using a colony plaque screen (Du Pont-New England Nuclear, Boston, Mass.) as described by the manufacturer's protocol to select for positive clones. Hybridizations were performed at 65° C. for 4 hours or overnight in 1% (w/v) SDS, 1M sodium chloride, and 10% dextran sulfate.

Screening of the λgt10 Libraries 1 and 2 yielded five positive clones. Clones BF1, -2, -3, and -6 were from Library 1, and clone BF8 was from Library 2.

The cDNA inserts from these clones were mapped by restriction endonuclease digestion with NotI enzyme and Southern analysis, the results of which are depicted schematically in FIG. 2. Enzyme digestions were carried out as described by the manufacturer. DNA fragments were separated by 1% agarose electrophoresis in TAE buffer and visualized by ethidium bromide staining and UV irradiation. DNA on selected gels was transferred to GENE SCREEN PLUS nylon membrane (Du Pont-New England Nuclear) in 10× SSC (1× SSC is 0.15M NaCl, 0.015M sodium citrate).

The blots were exposed to a UV light cross-linker (Stratagene) for 30 s and air-dried. Hybridizations were performed at 65° C. as described in the Du Pont-New England Nuclear protocol.

inserts from the λgt10 phages were purified and subcloned into pBluescript II(+) vector. Plasmid DNA was prepared as reported (Maniatis, et al., (1983), *Molecular Cloning: A Laboratory Manual*, Cold Spring Harbor Laboratory, Cold Spring Harbor, N.Y.) and further purified by polyethylene glycol precipitation (Titus, D. E. (ed) (1991) *Promega Protocols and Applications Guide*), 2nd Ed.) or by fast protein liquid chromatography (McClung, et al., *Anal Biochem* 177:378–382 (1989)). Double stranded plasmid DNA was used for sequencing on an ABI model 373A DNA sequencer using a fluorescent dye-labeled dideoxy terminator kit (ABI) and Taq polymerase (Perkin-Elmer Cetus). DNA sequences were determined by sequencing both strands of DNA inserts. DNA and the encoded protein sequences were analyzed with the computer program PC/GENE (IntelliGenetics).

Sequence analysis of the inserts in four clones (BF1, -2, -3 and -8) were identical, containing 1651 nucleotides and a poly(A) tail. However, the insert in clone BF6 was truncated by 551 base pairs on the 5'-end and 90 base pairs on the 3'-end. Sequence analysis indicated that Clone BF6 contained nucleotide sequences 800–1812 of TGase-H cDNA. The 3'-end contained a poly(A) tail, indicating an alternative polyadenylation site. Since the mRNA has an apparent size of 1.9 kb, and the longest insert obtained was 1.65 kb, it was concluded that the isolated clones contained incomplete cDNA sequences.

To obtain the complete 5' sequence of the 1.9-kb mRNA species, a primer extension experiment was performed. Three oligonucleotides were synthesized for use in a polymerase chain reaction (PCR) to obtain the missing 5'-end sequence of the incomplete cDNA clones. The first primer (P1) was composed of 21 nucleotide bases complementary to the 3'-end of BF6 clone. This sequence was not found in human cellular TGase cDNA and thus was unique to the new mRNA. The sequence of P1 is 5-dGGTCACTACCTAGCATGTTGT (SEQ ID NO:3).

The first strand cDNA was synthesized from the 1.9-kb size-selected mRNA isolated using an RN AID Kit (Bio101, La Jolla, Calif.). The gel-isolated mRNA was passed over an oligo(dT)-cellulose column to eliminate any inhibitors of the reverse transcriptase and then examined by Northern blot hybridization. Two micrograms of 1.9-kb size-selected mRNA was primed with 200 pmol of P1 using the copy kit (Invitrogen). The reaction was incubated at 42° C. for 1 hour, heated to 95° C. for 5 min, and immediately chilled on ice. One-fifth of the cDNA product was amplified with two additional primers (P2 and P3) in a Ericomp-Single Block System (San Diego, Calif.), in a final volume of 50 μl, as described previously. Buck, et al., *BioTechniques* 11, 636–639 (1991). The DNA/RNA hybrids were denatured at 94° C. for 1 minute and, after annealing, extended at 72° C. for 3 minutes for 45 cycles. Primer annealing for the first 5 cycles was at 37° C. for 2 minutes, and at 42° C. for 2 minutes for the final 40 cycles. A final 7-minute incubation at 72° C. was found to extend incomplete products. Primer 2 (P2), complementary to nucleotides 630–645 of clone BF8, was used as the downstream primer and primer 3 (P3), which was composed of nucleotides 3–23 of human cellular TGase cDNA, was used as an upstream primer. The sequences of P2 and P3 were 5-dAATTCGCGGCCGCGATGTCTAGGATCCCATCTTC (SEQ ID NO:4) and 5-dCAGGCGTGACGCCAGTTCTAA (SEQ ID NO:5), respectively.

Five microliters of the reaction product was electrophoresed on 1% agarose. Southern blot hybridization with a $^{32}$P-labeled 2.0-kb probe showed the specific band product consisting of 0.7 kb. The unmodified PCR products were directly cloned into T-vectors constructed from EcoRV-digested pBluescript II SK(−) as described previously (Marchuk, et al., *Nucleic Acids Res* 19:1154 (1991)) or directly cloned using the PCR 1000 Kit (Invitrogen).

From more than 200 transformants, 28 white colonies were chosen by color detection to make mini preparations of plasmid DNA. Digested DNA plasmid preparations were fractionated on 1% agarose, and positive clones were detected by Southern hybridization.

Sequence analysis revealed that one cloned PCR product (BF15) contained the additional 5' sequences. The BF15 clone consisted of nucleotides 1–710. The combined length of the inserts in clones BF1, -2, -3, and -8, and the extended 5' sequence yielded a full length of 1910 bp (not including the poly(A) tail). The full length of the 5'-extended clone BF6 yielded 1858 nucleotides. Thus, the transcripts would contain two mRNA species similar in size (1910 and 1858 bases). This agrees with the estimate of the 1.9 kb mRNA species from Northern analysis.

A full-length TGase-H cDNA clone was constructed by subcloning a 450-base pair BstXI fragment from clone BF15 containing the 5'-end of the TGase-H sequence into clone BF8 using pBluescript II SK(−). The complete nucleotide sequence of the TGase-H cDNA thus obtained, and the deduced amino acid sequence are shown in FIG. 1 and SEQ ID NO:2. The 1910-bp cDNA contained an open reading frame starting at nucleotide 133, encoding a polypeptide of 548 amino acids as compared with 687 amino acids for the cellular TGase. The nucleotide sequence CGACCATGG around the initiation site is similar to the consensus sequence for initiation usually found in higher eukaryotes. The 3'-untranslated region is relatively short, containing only 90 nucleotides in clone BF6 and 180 nucleotides in the remaining clones. The typical polyadenylation signal AATAAA was not present in the BF6 cDNA, whereas a putative TATAAA sequence was found at nucleotides 1891–1896 in the other cDNA clones.

The TGase-H cDNA sequence from nucleotides 1–1747 exhibits 98% identity when aligned with the 5'-end of the cellular TGase cDNA. However, downstream of this point, the sequence diverges and is followed shortly by a termination codon in the TGase-H cDNA. At the divergence point (base 1748), there is an intron-exon consensus border sequence CTGGTAA. Genomic Southern analysis of HEL cells' DNA with the 4.0-kb TGase and 1.9-kb TGase-H cDNA probes showed that all bands detected with the smaller probe were also detected by the larger probe. Taken together, these data suggest that both transcripts are produced by alternative splicing from a single gene.

Comparison of deduced amino acid sequences also show a high degree of identity (98%) between the TGase-H and the cellular TGase. The active site Cysteine (277) and the putative $Ca^{2+}$ binding region between amino acids 446–453 were conserved. A total of 14 base changes were found. Ten of the base changes were in the coding region, most of which were silent, resulting in only five amino acid changes. The derived amino acid composition for TGase-H was compared with other transglutaminases (Table I). Only a secretory transglutaminase from the coagulating gland of the rat (CGS-TGase), with an SDS molecular mass of 65 kD, is similar in size to TGase-H, as compared with the TGase-H. Although some amino acids were similar in composition (i.e., both have 19 cysteines), overall the amino acid composition was different.

The predicted isoelectric point (pI) of TGase-H is 4.84, similar to human cellular TGase (pI=4.95) and guinea pig TGase (pI=4.92). However, other transglutaminases, particularly the extracellular enzymes (Table I), exhibited higher isoelectric points.

In spite of the approximate 147 amino acids missing in TGase-H when compared with the cellular TGase, the isoelectric points for both proteins are similar. This may reflect the amino acid sequence at the carboxyl-terminal of the cellular TGase may not have a drastic effect on the tertiary structure of the enzyme.

EXAMPLE 3

Transcription and Translation of cDNA

The predicted open reading frame of TGase-H should encode a protein product with a molecular weight of approximately 61,740. To verify the existence of this reading frame, TGase-H mRNA was synthesized in vitro from the cDNA and was then translated by an in vitro system. Translation of the lysate with no added synthetic mRNA produced no protein bands. Translation of a TGase-H sense transcript produced one protein band of approximately 63 kD, as expected.

For transcription in the sense orientation, the TGase-H cDNA was linearized with HindIII and transcribed from the Triiodothyronine promoter of the Bluescript vector using triiodothyronine RNA polymerase and Stratagene mRNA capping kit. One and one-half micrograms of capped mRNA transcripts were translated in a 50-μl reaction mixture containing 35 μl of rabbit reticulocyte lysate (Promega, Madison, Wis.), 0.05 mM each of 19 amino acids, and 50 mCi of [$^{35}$S]methionine (1078 Ci/mmol, Du Pont-New England Nuclear). The reaction was incubated at 30° C. for 1h. Five microliters of the reaction mixture was diluted to 25 μl with SDS-PAGE loading buffer (0.06M Tris, pH 6.8, 5% glycerol, 1% SDS, 5% 2-mercaptoethanol, and 0.01% bromphenol blue), and heated for 3 minutes at 100° C. A 5-μl aliquot was removed for SDS-PAGE, and the remainder was stored at −20° C.

EXAMPLE 4

Immunoprecipitation of Translation Products

In vitro and in vivo translation products of TGase-H were immunoprecipitated as described previously (Fraij, B. M., Clin Chem 35:658–662 (1989)). For the in vitro product, 50 μl of the [$^{35}$S]methionine in vitro reaction product was mixed with 50 μl of phosphate-buffered isotonic saline (PBS) and 50 μl of rabbit anti-human erythrocyte transglutaminase antibody. Gelatin was added to a final concentration of 0.16%.

For in vivo product, HEL cell suspensions ($10^6$ cells) were lysed in TBS buffer (0.04M Tris, pH 7.5, 0.15M NaCl. After centrifugation, 0.5 μl of supernatant was mixed with 50 μl of rabbit anti-human erythrocyte transglutaminase. Gelatin was added to 0.16% total volume. Each mixture was incubated overnight at 4° C., after which 100 μl of protein A suspension in PBS (Bethesda Research Laboratories) was added. The mixtures were placed on a shaker at room temperature for 2 hours and then the pellets were recovered by centrifugation for 2 minutes. The pellets were washed four times with PBS containing 0.1% SDS. The washed pellets were resuspended in 25 μl of SDS-PAGE loading buffer, placed in a boiling water bath for 5 min, cooled, and centrifuged. The supernatant was removed and 5 μl was used for SDS-PAGE electrophoresis.

The immunoprecipitation products and the reticulocyte lysate in vitro translation mixture were separated by SDS-polyacrylamide gel electrophoresis using a 4% stacking gel and a 10% separating gel. The gels were treated with a fluorographic enhancer (Du Pont-New England Nuclear) and exposed to Kodak XAR-2 film. For Western blot analysis, proteins were transferred by electrophoresis to an IMMOBILON membrane and then detected with rabbit anti-human erythrocyte transglutaminase antibody and a peroxidase-conjugated anti-rabbit IgG detection kit (Bio-Rad).

Monoclonal antibody (CUB 74) against guinea pig liver transglutaminase and a polyclonal antiserum against human erythrocyte transglutaminase were used to perform the immunoprecipitations. A strong TGase-H band of 63 kD was detected with the polyclonal antibody, whereas a weak band was detected with the monoclonal antibody. Normal serum produced a clear background. These data are consistent with a high degree of identity between TGase-H and the cellular TGase protein sequence.

Immunoprecipitation of total protein from cultured HEL cells was assayed using the polyclonal antibody. A clear band of the correct size for TGase-H was seen in the immunoprecipitate of cell lysate material stained with the anti-human erythrocyte transglutaminase antibody. There was no such band in the immunoprecipitate of cell lysate with normal serum. A heavy staining band of approximately 53 kD was observed which represents the heavy chains of IgG molecules. A cellular TGase band of about 82 kD was also observed. The radioactively labeled protein from the in vitro translation reaction using TGase-H mRNA was also immunoprecipitated by the polyclonal antibody. This protein was indistinguishable in size from a protein produced in vivo by HEL cells. Thus, a major glycosylation or post-translational modification of TGase-H is not likely.

EXAMPLE 5

Expression of TGase-H

Northern analysis of HEL cells showed the expression of a 4.0- and a 1.9-kb band. Isolated preparations of poly(A)$^+$ RNA from normal human fibroblast cells WI-38 and from HEL cells were subjected to RNA blot analysis. The 4.0-kb band was found in both HEL and normal cells. However, the 1.9-kb band was expressed at a much lower level in the normal cells where the relative abundance of the 4.0- and 1.9-kb RNA species was about 7:1.

EXAMPLE 6

Bacterial Expression of TGase-H and Resulting Activity Data cDNA sequence and pET system In order to obtain native TGase-H without the 4.5 kD leader peptide of the pRSET plasmid, a pET system was used. The native, natural human TGase-H protein which was encoded by the cloned cDNA was produced in two bacterial expression systems pET-14b and pET-15b (Novagen).

TGase-H cDNA in the pRSET vector was digested with two restriction enzymes, NcoI and XhoI for 2 hours as recommended by the supplier (Promega). A fragment of about 1.78 kb was then purified from a 1% agarose gel. pET 14-b and 15-b vectors from Novagen were also digested with NcoI and XhoI to release the DNA sequence which codes for His-Tag leader peptide. Thus, the inserted TGase-H cDNA will translate into the native encoded protein. After the pET DNA was purified from 1% agarose gel, pET DNA and TGase-H cDNA were ligated by T4 DNA ligase as recommended (Promega). pET 14-b and pET 15-b plasmids contain the T7 promotor to drive expression. In addition, pET 15-b contains the lac operator and requires isopropyl -β-D-thiogalacto-pyranoside (IPTG) for induction and expression of the protein.

Protocol for TGase-H active expression

A commercially-available expression vector was purchased from Novagen, and the manufacturer's protocol modified to reduce the amount expression of TGase-H in inclusion bodies. pET 14-b and pET 15-b containing TGase-H cDNA were introduced into BL21 (Novagen) bacterial cells according to supplier's protocol. Bacterial plates were kept at 4° C. while glycerol stocks of the cells were kept at −80° C. A single colony was picked from the plate for overnight culture at 37° C. in LB-media, containing 0.047M carbenicillin. For the pET 15-b construct, the overnight culture was diluted 1:50 with fresh LB-media containing carbenicillin. Cells were grown at 37° C. and 1 mM IPTG was added when the optical density (600 nm) reached 0.3. Cells were harvested between 5–19 hrs. Cells were sedimented for 5 minutes at 6000 rpm and the pellet resuspended in deionized H$_2$O containing 0.3 mg lysozyme/ml. After incubation at 37° C. for 15 minutes the cells were exposed to several freezing and thawing cycles until the resulting liquid was viscous. Sonication was carried out for 10 seconds three times. Centrifugation was performed and both supernatant and pellet were stored.

Enzyme activity was determined by C$^{14}$-putrescine incorporation into dimethylated casein; Lorand, et al., "A filter paper assay for transaminating enzymes using radioactive amine substrates," *Analytical Biochemistry* 50:623 (1972). All assays were performed on the supernatant of cell lysates.

TABLE III

Activity Assay for Standard Expression Protocol (IPTG Induction) and Media.

| Sample 45 µL of bacterial lysate (2 µg/µL) | Final Ca$^{++}$ Concentration (mM) | Sample Identification | Dpm/1 hr rxn |
|---|---|---|---|
| 1 | 0 (EDTA) | pET 14-b TGase-H | 301 |
| 2 | 0.1 | pET 14-b TGase-H | 281 |
| 3 | 1.0 | pET 14-b TGase-H | 3285 |
| 4 | 5.0 | pET 14-b TGase-H | 6478 |
| 5 | 0 (EDTA) | pET 15-b TGase-H | 298 |
| 6 | 0.1 | pET 15-b TGase-H | 419 |
| 7 | 1.0 | pET 15-b TGase-H | 247 |
| 8 | 5.0 | pET 15-b TGase-H | 599 |
| 9 | 0 (EDTA) | puc19 (control) | 304 |
| 10 | 5 | puc19 (control) | 189 |

Expression with pET 15-b requires IPTG. Because it gave poor results, the following data was obtained with pET 14-b without IPTG induction.

Bacterial growth media modification

LB media was purchased commercially and modified by the addition of yeast extract, phosphate, and/or glycerol as follows. Three media were produced.

LB+Y: final volume 50 ml.
0.5 g. tryptone
0.25 g. yeast extract
0.5 g. NaCl
5 mls of PO$_4$ mix (0.17M KH$_2$PO$_4$, 0.7M K$_2$PO$_4$)
1 g. of yeast extract (1.25 g/50 ml.)

LB+G: final volume 50 ml.
0.5 g. tryptone
0.25 g. yeast extract
0.5 g. NaCl
5 mls of PO$_4$ mix (0.17M KH$_2$PO$_4$, 0.7M K$_2$PO$_4$)
400 µl of a 50% glycerol solution.

LB+G+Y: final volume 50 ml.
0.5 g. tryptone
0.25 g. yeast extract
0.5 g. NaCl
5 mls of PO$_4$ mix (0.17M KH$_2$PO$_4$, 0.7M K$_2$PO$_4$)
1 g. of yeast extract (1.25 g/50 ml.)
400 µl of a 50% glycerol solution.

TABLE IV

Activity data with media modifications and no IPTG. 45 µL/assay for 1 hr 37° C. (2 µg/µL total protein).

| Sample | DPM |
|---|---|
| LB | 1120 |
| LB + Y | 8873 |
| LB + G | 3375 |
| LB + G + Y | 4645 |

The yeast extract made cells produce more active TGase-H probably because fewer inclusion bodies were formed, thus more soluble TGase-H enzyme was produced.

TABLE V

Activity data with yeast extract added to media, no IPTG, and bacterial culture growth temperature lowered to 30° C.

| Sample | DPM | DPM |
|--------|-----|-----|
| LBY | 33,260 (2 hrs) | 15,600 (1 hr) |
| LB | 16,800 (2 hrs) | 8,200 (1 hr) |

When LB+yeast culture were incubated at 30° C. overnight, there was a two-fold increase in TGase-H activity. 45 μL of bacterial lysate of 2 μg/μL total protein. Assay reaction time either 1 hr or 2 hrs at 37° C.

Western blots show that TGase-H from LB+yeast at 30° C. incubation increased the soluble TGase-H. An equal amount of total protein (bacterial lysate) was applied to each lane 5 μL (microliter). The results from TGase-H immuno-detection and TGase-H activity by radioactive assay both support that more TGase-H in LB+Y culture was soluble enzyme and also TGase-H enzyme activity was obtained.

The above description is intended to be illustrative of the invention, and is not intended to limit the invention in any manner. As is readily apparent to those skilled in the art, other materials may be substituted for those disclosed and still be within the scope and spirit of the invention.

We claim:

1. A purified human tissue transglutaminase encoded by a cDNA of about 1.9 kilobases transcribed from an RNA transcript indigenous to human erythroleukemia cells.

2. The purified human tissue transglutaminase of claim 1, wherein the molecular weight is about 63,000 daltons.

3. A purified tissue transglutaminase comprising the amino acid sequence depicted in SEQ ID NO:2.

4. A purified TGase-H enzyme prepared by a process comprising the following steps:

(a) purifying a cDNA encoding the amino acid sequence depicted in SEQ ID NO:2;

(b) constructing an expression vector for TGase-H comprising the cDNA encoding the amino acid sequence depicted in SEQ ID NO:2;

(c) transforming a bacterial host cell with the expression vector of step (b);

(d) culturing the bacterial host cell of step (c) under conditions allowing expression of the TGase-H enzyme; and (e) purifying the TGase-H from the cultured bacterial host cell.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1910 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( G ) CELL TYPE: Human Erythroleukemia Cells
        ( H ) CELL LINE: GM06141A ( v i i ) IMMEDIATE SOURCE:
        ( A ) LIBRARY: Library of B. Fraij
        ( B ) CLONE: TGase-H ( i x ) FEATURE:
        ( A ) NAME/KEY: CDS
        ( B ) LOCATION: 133..1779
        ( C ) IDENTIFICATION METHOD: experimental
        ( D ) OTHER INFORMATION: /product="TISSUE TRANSGLUTAMINASE
            HOMOLOGUE"
            / evidence=EXPERIMENTAL
            / citation=([1])

( x ) PUBLICATION INFORMATION:
        ( A ) AUTHORS: Fraij, Bassam M
            Birckbichler, Paul J
            Jr. Patterson, Manford K
            Gonzales, Robert A
        ( B ) TITLE: A Retinoic Acid-inducible mRNA from Human
            Erythroleukemia Cells Encodes a Novel Tissue
            Transglutaminase Homologue
        ( C ) JOURNAL: J. Biol. Chem.
        ( D ) VOLUME: 267
        ( G ) DATE: 1992
        ( K ) RELEVANT RESIDUES IN SEQ ID NO:1: FROM 1 TO 1910

( x ) PUBLICATION INFORMATION:
        ( A ) AUTHORS: Fraij, Bassam M
            Birckbichler, Paul J
            Jr. Patterson, Manford K
            Gonzales, Robert A
        ( B ) TITLE: A Novel Human Tissue Transglutaminase
            Homologue from Erythroleukemia Cells (C) JOURNAL: Conference
(G) DATE: 6-7-1992

(xi) SEQUENCE DESCRIPTION: SEQ ID NO:1:

```
CAGGCGTGAC GCCAGTTCTA AATCTTGAAA CAGAACAAAA CTTCAAAGTA CACCAAAATA                 60

GAACCTCCTT AAAGCATAAA TCTCACGGAG GGTCTCGCCG CCAGTGGAAG GAGCCACCGC                120

CCCCGCCCGA CC ATG GCC GAG GAG CTG GTC TTA GAG AGG TGT GAT CTG                    168
              Met Ala Glu Glu Leu Val Leu Glu Arg Cys Asp Leu
                1               5                       10

GAG CTG GAG ACC AAT GGC CGA GAC CAC CAC ACG GCC GAC CTG TGC CGG                  216
Glu Leu Glu Thr Asn Gly Arg Asp His His Thr Ala Asp Leu Cys Arg
        15                  20                  25

GAG AAG CTG GTG GTG CGA CGG GGC CAG CCC TTC TGG CTG ACC CTG CAC                  264
Glu Lys Leu Val Val Arg Arg Gly Gln Pro Phe Trp Leu Thr Leu His
    30                  35                  40

TTT GAG GGC CGC AAC TAC GAG GCC AGT GTA GAC AGT CTC ACC TTC AGT                  312
Phe Glu Gly Arg Asn Tyr Glu Ala Ser Val Asp Ser Leu Thr Phe Ser
45                  50                  55                  60

GTC GTG ACC GGC CCA GCC CCT AGC CAG GAG GCC GGG ACC AAG GCC CGT                  360
Val Val Thr Gly Pro Ala Pro Ser Gln Glu Ala Gly Thr Lys Ala Arg
                65                  70                  75

TTT CCA CTA AGA GAT GCT GTG GAG GAG GGT GAC TGG ACA GCC ACC GTG                  408
Phe Pro Leu Arg Asp Ala Val Glu Glu Gly Asp Trp Thr Ala Thr Val
            80                  85                  90

GTG GAC CAG CAA GAC TGC ACC CTC TCG CTG CAG CTC ACC ACC CCG GCC                  456
Val Asp Gln Gln Asp Cys Thr Leu Ser Leu Gln Leu Thr Thr Pro Ala
                95                  100                 105

AAC GCC CCC ATC GGC CTG TAT CGC CTC AGC CTG GAG GCC TCC ACT GGC                  504
Asn Ala Pro Ile Gly Leu Tyr Arg Leu Ser Leu Glu Ala Ser Thr Gly
    110                 115                 120

TAC CAG GGA TCC AGC TTT GTG CTG GGC CAC TTC ATT TTG CTC TTC AAC                  552
Tyr Gln Gly Ser Ser Phe Val Leu Gly His Phe Ile Leu Leu Phe Asn
125                 130                 135                 140

GCC TGG TGC CCA GCG GAT GCT GTG TAC CTG GAC TCG GAA GAG GAG CGG                  600
Ala Trp Cys Pro Ala Asp Ala Val Tyr Leu Asp Ser Glu Glu Glu Arg
                145                 150                 155

CAG GAG TAT GTC CTC ACC CAG CAG GGC TTT ATC TAC CAG GGC TCG GCC                  648
Gln Glu Tyr Val Leu Thr Gln Gln Gly Phe Ile Tyr Gln Gly Ser Ala
                160                 165                 170

AAG TTC ATC AAG AAC ATA CCT TGG AAT TTT GGG CAG TTT GAA GAT GGG                  696
Lys Phe Ile Lys Asn Ile Pro Trp Asn Phe Gly Gln Phe Glu Asp Gly
    175                 180                 185

ATC CTA GAC ATC TGC CTG ATC CTT CTA GAT GTC AAC CCC AAG TTC CTG                  744
Ile Leu Asp Ile Cys Leu Ile Leu Leu Asp Val Asn Pro Lys Phe Leu
    190                 195                 200

AAG AAC GCC GGC CGT GAC TGC TCC CGC CGC AGC AGC CCC GTC TAC GTG                  792
Lys Asn Ala Gly Arg Asp Cys Ser Arg Arg Ser Ser Pro Val Tyr Val
205                 210                 215                 220

GGC CGG GTG GTG AGT GGC ATG GTC AAC TGC AAC GAT GAC CAG GGT GTG                  840
Gly Arg Val Val Ser Gly Met Val Asn Cys Asn Asp Asp Gln Gly Val
                225                 230                 235

CTG CTG GGA CGC TGG GAC AAC AAC TAC GGG GAC GGC GTC AGC CCC ATG                  888
Leu Leu Gly Arg Trp Asp Asn Asn Tyr Gly Asp Gly Val Ser Pro Met
            240                 245                 250

TCC TGG ATC GGC AGC GTG GAC ATC CTG CGG CGC TGG AAG AAC CAC GGC                  936
Ser Trp Ile Gly Ser Val Asp Ile Leu Arg Arg Trp Lys Asn His Gly
                255                 260                 265

TGC CAG CGC GTC AAG TAT GGC CAG TGC TGG GTC TTC GCC GCC GTG GCC                  984
Cys Gln Arg Val Lys Tyr Gly Gln Cys Trp Val Phe Ala Ala Val Ala
    270                 275                 280
```

```
TGC ACA GTG CTG AGG TGC CTG GGC ATC CCT ACC CGC GTC GTG ACC AAC    1032
Cys Thr Val Leu Arg Cys Leu Gly Ile Pro Thr Arg Val Val Thr Asn
285             290             295             300

TAC AAC TCG GCC CAT GAC CAG AAC AGC AAC CTT CTC ATC GAG TAC TTC    1080
Tyr Asn Ser Ala His Asp Gln Asn Ser Asn Leu Leu Ile Glu Tyr Phe
            305             310             315

CGC AAT GAG TTT GGG GAG ATC CAG GGT GAC AAG AGC GAG ATG ATC TGG    1128
Arg Asn Glu Phe Gly Glu Ile Gln Gly Asp Lys Ser Glu Met Ile Trp
        320             325             330

AAC TTC CAC TGC TGG GTG GAG TCG TGG ATG ACC AGG CCG GAC CTG CAG    1176
Asn Phe His Cys Trp Val Glu Ser Trp Met Thr Arg Pro Asp Leu Gln
        335             340             345

CCG GGG TAC GAG GGC TGG CAG GCC CTG GAC CCA ACG CCC CAG GAG AAG    1224
Pro Gly Tyr Glu Gly Trp Gln Ala Leu Asp Pro Thr Pro Gln Glu Lys
    350             355             360

AGC GAA GGG ACG TAC TGC TGT GGC CCA GTT CCA GTT CGT GCC ATC AAG    1272
Ser Glu Gly Thr Tyr Cys Cys Gly Pro Val Pro Val Arg Ala Ile Lys
365             370             375             380

GAG GGC GAC CTG AGC ACC AAG TAC GAT GCG CCC TTT GTC TTT GCG GAG    1320
Glu Gly Asp Leu Ser Thr Lys Tyr Asp Ala Pro Phe Val Phe Ala Glu
            385             390             395

GTC AAT GCC GAC GTG GTA GAC TGG ATC CAG CAG GAC GAT GGG TCT GTG    1368
Val Asn Ala Asp Val Val Asp Trp Ile Gln Gln Asp Asp Gly Ser Val
        400             405             410

CAC AAA TCC ATC AAC CGT TCC CTG ATC GTT GGG CTG AAG ATC AGC ACT    1416
His Lys Ser Ile Asn Arg Ser Leu Ile Val Gly Leu Lys Ile Ser Thr
        415             420             425

AAG AGC GTG GGC CGA GAC GAG CGG GAG GAT ATC ACC CAC ACC TAC AAA    1464
Lys Ser Val Gly Arg Asp Glu Arg Glu Asp Ile Thr His Thr Tyr Lys
    430             435             440

TAC CCA GAG GGG TCC TCA GAG GAG AGG GAG GCC TTC ACA AGG GCG AAC    1512
Tyr Pro Glu Gly Ser Ser Glu Glu Arg Glu Ala Phe Thr Arg Ala Asn
445             450             455             460

CAC CTG AAC AAA CTG GCC GAG AAG GAG GAG ACA GGG ATG GCC ATG CGG    1560
His Leu Asn Lys Leu Ala Glu Lys Glu Glu Thr Gly Met Ala Met Arg
            465             470             475

ATC CGT GTG GGC CAG AGC ATG AAC ATG GGC AGT GAC TTT GAC GTC TTT    1608
Ile Arg Val Gly Gln Ser Met Asn Met Gly Ser Asp Phe Asp Val Phe
        480             485             490

GCC CAC ATC ACC AAC AAC ACC GCT GAG GAG TAC GTC TGC CGC CTC CTG    1656
Ala His Ile Thr Asn Asn Thr Ala Glu Glu Tyr Val Cys Arg Leu Leu
        495             500             505

CTC TGT GCC CGC ACC GTC AGC TAC AAT GGG ATC TTG GGG CCC GAG TGT    1704
Leu Cys Ala Arg Thr Val Ser Tyr Asn Gly Ile Leu Gly Pro Glu Cys
    510             515             520

GGC ACC AAG TAC CTG CTC AAC CTC AAC CTG GAG CCT TTC TCT GGT AAA    1752
Gly Thr Lys Tyr Leu Leu Asn Leu Asn Leu Glu Pro Phe Ser Gly Lys
525             530             535             540

GCC CTG TGT TCC TGG AGC ATT TGT TGACCGCCAA CTGACAACAT GCTAGGTAGT    1806
Ala Leu Cys Ser Trp Ser Ile Cys
            545

GACCTAACCA CTTAGCATGT GTGATTTCAC CCCACAGACA CTTACATGGC GCTGACTCTG    1866

GGGCAGGCCC TGTCCTAAGC ACTTTATAAA TATCAACCCA CTTA                    1910
```

( 2 ) INFORMATION FOR SEQ ID NO:2:

( i ) SEQUENCE CHARACTERISTICS:
        ( A ) LENGTH: 548 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Glu | Glu | Leu | Val | Leu | Glu | Arg | Cys | Asp | Leu | Glu | Leu | Glu | Thr |
|---|---|---|---|---|---|---|---|---|---|---|---|---|---|---|---|
| 1 | | | | 5 | | | | | 10 | | | | | 15 | |
| Asn | Gly | Arg | Asp | His | His | Thr | Ala | Asp | Leu | Cys | Arg | Glu | Lys | Leu | Val |
| | | | 20 | | | | | 25 | | | | | 30 | | |
| Val | Arg | Arg | Gly | Gln | Pro | Phe | Trp | Leu | Thr | Leu | His | Phe | Glu | Gly | Arg |
| | | 35 | | | | | 40 | | | | | 45 | | | |
| Asn | Tyr | Glu | Ala | Ser | Val | Asp | Ser | Leu | Thr | Phe | Ser | Val | Val | Thr | Gly |
| | 50 | | | | | 55 | | | | | 60 | | | | |
| Pro | Ala | Pro | Ser | Gln | Glu | Ala | Gly | Thr | Lys | Ala | Arg | Phe | Pro | Leu | Arg |
| 65 | | | | | 70 | | | | 75 | | | | | | 80 |
| Asp | Ala | Val | Glu | Glu | Gly | Asp | Trp | Thr | Ala | Thr | Val | Val | Asp | Gln | Gln |
| | | | | 85 | | | | | 90 | | | | | 95 | |
| Asp | Cys | Thr | Leu | Ser | Leu | Gln | Leu | Thr | Thr | Pro | Ala | Asn | Ala | Pro | Ile |
| | | | 100 | | | | | 105 | | | | | 110 | | |
| Gly | Leu | Tyr | Arg | Leu | Ser | Leu | Glu | Ala | Ser | Thr | Gly | Tyr | Gln | Gly | Ser |
| | | 115 | | | | | 120 | | | | | 125 | | | |
| Ser | Phe | Val | Leu | Gly | His | Phe | Ile | Leu | Leu | Phe | Asn | Ala | Trp | Cys | Pro |
| | 130 | | | | | 135 | | | | | 140 | | | | |
| Ala | Asp | Ala | Val | Tyr | Leu | Asp | Ser | Glu | Glu | Glu | Arg | Gln | Glu | Tyr | Val |
| 145 | | | | | 150 | | | | | 155 | | | | | 160 |
| Leu | Thr | Gln | Gln | Gly | Phe | Ile | Tyr | Gln | Gly | Ser | Ala | Lys | Phe | Ile | Lys |
| | | | | 165 | | | | | 170 | | | | | 175 | |
| Asn | Ile | Pro | Trp | Asn | Phe | Gly | Gln | Phe | Glu | Asp | Gly | Ile | Leu | Asp | Ile |
| | | | 180 | | | | | 185 | | | | | 190 | | |
| Cys | Leu | Ile | Leu | Leu | Asp | Val | Asn | Pro | Lys | Phe | Leu | Lys | Asn | Ala | Gly |
| | | 195 | | | | | 200 | | | | | 205 | | | |
| Arg | Asp | Cys | Ser | Arg | Arg | Ser | Ser | Pro | Val | Tyr | Val | Gly | Arg | Val | Val |
| | 210 | | | | | 215 | | | | | 220 | | | | |
| Ser | Gly | Met | Val | Asn | Cys | Asn | Asp | Asp | Gln | Gly | Val | Leu | Leu | Gly | Arg |
| 225 | | | | | 230 | | | | | 235 | | | | | 240 |
| Trp | Asp | Asn | Asn | Tyr | Gly | Asp | Gly | Val | Ser | Pro | Met | Ser | Trp | Ile | Gly |
| | | | | 245 | | | | | 250 | | | | | 255 | |
| Ser | Val | Asp | Ile | Leu | Arg | Arg | Trp | Lys | Asn | His | Gly | Cys | Gln | Arg | Val |
| | | | 260 | | | | | 265 | | | | | 270 | | |
| Lys | Tyr | Gly | Gln | Cys | Trp | Val | Phe | Ala | Ala | Val | Ala | Cys | Thr | Val | Leu |
| | | 275 | | | | | 280 | | | | | 285 | | | |
| Arg | Cys | Leu | Gly | Ile | Pro | Thr | Arg | Val | Val | Thr | Asn | Tyr | Asn | Ser | Ala |
| | 290 | | | | | 295 | | | | | 300 | | | | |
| His | Asp | Gln | Asn | Ser | Asn | Leu | Leu | Ile | Glu | Tyr | Phe | Arg | Asn | Glu | Phe |
| 305 | | | | | 310 | | | | | 315 | | | | | 320 |
| Gly | Glu | Ile | Gln | Gly | Asp | Lys | Ser | Glu | Met | Ile | Trp | Asn | Phe | His | Cys |
| | | | | 325 | | | | | 330 | | | | | 335 | |
| Trp | Val | Glu | Ser | Trp | Met | Thr | Arg | Pro | Asp | Leu | Gln | Pro | Gly | Tyr | Glu |
| | | | 340 | | | | | 345 | | | | | 350 | | |
| Gly | Trp | Gln | Ala | Leu | Asp | Pro | Thr | Pro | Gln | Glu | Lys | Ser | Glu | Gly | Thr |
| | | 355 | | | | | 360 | | | | | 365 | | | |
| Tyr | Cys | Cys | Gly | Pro | Val | Pro | Val | Arg | Ala | Ile | Lys | Glu | Gly | Asp | Leu |
| | 370 | | | | | 375 | | | | | 380 | | | | |
| Ser | Thr | Lys | Tyr | Asp | Ala | Pro | Phe | Val | Phe | Ala | Glu | Val | Asn | Ala | Asp |
| 385 | | | | | 390 | | | | | 395 | | | | | 400 |

| Val | Val | Asp | Trp | Ile<br>405 | Gln | Gln | Asp | Asp<br>410 | Gly | Ser | Val | His | Lys | Ser<br>415 | Ile |
| Asn | Arg | Ser | Leu<br>420 | Ile | Val | Gly | Leu | Lys<br>425 | Ile | Ser | Thr | Lys | Ser<br>430 | Val | Gly |
| Arg | Asp | Glu<br>435 | Arg | Glu | Asp | Ile | Thr<br>440 | His | Thr | Tyr | Lys | Tyr<br>445 | Pro | Glu | Gly |
| Ser | Ser<br>450 | Glu | Glu | Arg | Glu | Ala<br>455 | Phe | Thr | Arg | Ala | Asn<br>460 | His | Leu | Asn | Lys |
| Leu<br>465 | Ala | Glu | Lys | Glu | Glu<br>470 | Thr | Gly | Met | Ala | Met<br>475 | Arg | Ile | Arg | Val | Gly<br>480 |
| Gln | Ser | Met | Asn | Met<br>485 | Gly | Ser | Asp | Phe | Asp<br>490 | Val | Phe | Ala | His | Ile<br>495 | Thr |
| Asn | Asn | Thr | Ala<br>500 | Glu | Glu | Tyr | Val | Cys<br>505 | Arg | Leu | Leu | Leu<br>510 | Cys | Ala | Arg |
| Thr | Val | Ser<br>515 | Tyr | Asn | Gly | Ile | Leu<br>520 | Gly | Pro | Glu | Cys<br>525 | Gly | Thr | Lys | Tyr |
| Leu | Leu<br>530 | Asn | Leu | Asn | Leu | Glu<br>535 | Pro | Phe | Ser | Gly | Lys<br>540 | Ala | Leu | Cys | Ser |
| Trp<br>545 | Ser | Ile | Cys | | | | | | | | | | | | |

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGTCACTACC TAGCATGTTG T        21

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

AATTCGCGGC CGCGATGTCT AGGATCCCAT CTTC        34

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CAGGCGTGAC GCCAGTTCTA A        21

(2) INFORMATION FOR SEQ ID NO:6:

(i) SEQUENCE CHARACTERISTICS:
        (A) LENGTH: 15 amino acids

```
            ( B ) TYPE: amino acid
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:
            ( A ) ORGANISM: Homo sapiens ( x i ) SEQUENCE DESCRIPTION: SEQ ID NO:6:

Ala Glu Glu Leu Val Leu Glu Arg Xaa Asp Leu Glu Leu Glu Thr
         1           5                  10                  15
```